United States Patent
Blain

(10) Patent No.: US 9,504,583 B2
(45) Date of Patent: Nov. 29, 2016

(54) IMPLANT AND METHOD FOR FACET IMMOBILIZATION

(75) Inventor: Jason Blain, Encinitas, CA (US)

(73) Assignee: Spinal Elements, Inc., Carlsbad, CA (US)

( * ) Notice: Subject to any disclaimer, the term of this patent is extended or adjusted under 35 U.S.C. 154(b) by 1050 days.

(21) Appl. No.: 12/106,248

(22) Filed: Apr. 18, 2008

(65) Prior Publication Data

US 2009/0264928 A1 Oct. 22, 2009
US 2012/0046695 A9 Feb. 23, 2012

Related U.S. Application Data

(63) Continuation-in-part of application No. 10/865,073, filed on Jun. 10, 2004, now Pat. No. 7,846,183.

(51) Int. Cl.
*A61B 17/70* (2006.01)
*A61F 2/44* (2006.01)
(Continued)

(52) U.S. Cl.
CPC ......... *A61F 2/4405* (2013.01); *A61B 17/7064* (2013.01); *A61F 2/28* (2013.01); *A61F 2002/2821* (2013.01); *A61F 2002/302* (2013.01); *A61F 2002/30446* (2013.01); *A61F 2002/30462* (2013.01); *A61F 2002/30507* (2013.01); *A61F 2002/30512* (2013.01); *A61F 2002/30754* (2013.01); *A61F 2002/30777* (2013.01); *A61F 2002/30968* (2013.01); *A61F 2220/0025* (2013.01); *A61F 2220/0041* (2013.01); *A61F 2220/0075* (2013.01); *A61F 2230/0065* (2013.01); *A61F 2310/00017* (2013.01); *A61F 2310/00023* (2013.01);
(Continued)

(58) Field of Classification Search
CPC ............... A61F 2/4405; A61F 2/4455; A61F 2002/30578; A61F 2002/2835; A61F 2002/30433; A61F 2002/30472; A61F 2002/30462; A61F 2220/0075; A61F 2220/0041; A61B 17/7062; A61B 17/7064; A61B 17/7022; A61B 17/7053; A61B 17/7071; A61B 17/8095
USPC .................................................. 606/246–250
See application file for complete search history.

(56) References Cited

U.S. PATENT DOCUMENTS 6,007,580 A * 12/1999 Lehto .................. A61F 2/30721
623/18.11
6,056,749 A * 5/2000 Kuslich ................ A61B 17/025
606/247
(Continued)

FOREIGN PATENT DOCUMENTS

DE 10135771 A1 * 2/2003
WO WO 2005076974 A2 * 8/2005

OTHER PUBLICATIONS

International Search Report for International App. No. PCT/US2009/040559, dated Jun. 8, 2009.
(Continued)

*Primary Examiner* — Lynnsy Summitt

(57) ABSTRACT

Devices and methods are provided for immobilizing facet joints of the vertebral column. Embodiments of the invention provide an implant that is inserted in a facet joint from which cartilage has been removed, and which retains the approximate original spacing of the facets in the joint. A retaining arrangement, such as an adhesive, a threaded fastener, or a screw is then used to secure the implant in the joint.

20 Claims, 11 Drawing Sheets

(51) Int. Cl.
*A61F 2/28* (2006.01)
*A61F 2/30* (2006.01)

(52) U.S. Cl.
CPC ............... *A61F 2310/00029* (2013.01); *A61F 2310/00203* (2013.01); *A61F 2310/00239* (2013.01); *A61F 2310/00317* (2013.01); *A61F 2310/00359* (2013.01)

(56) References Cited

U.S. PATENT DOCUMENTS

| | | | | |
|---|---|---|---|---|
| 6,966,930 | B2* | 11/2005 | Arnin | A61B 17/562 606/247 |
| 6,974,478 | B2* | 12/2005 | Reiley et al. | 623/17.11 |
| 7,037,342 | B2* | 5/2006 | Nilsson | A61L 27/58 623/18.11 |
| 7,087,084 | B2* | 8/2006 | Reiley | 623/17.11 |
| 7,799,053 | B2* | 9/2010 | Haid, Jr. | A61B 17/7064 606/246 |
| 2002/0151895 | A1* | 10/2002 | Soboleski | A61B 17/7064 606/247 |
| 2003/0045936 | A1* | 3/2003 | Angelucci | A61B 17/7059 623/17.11 |
| 2004/0111093 | A1* | 6/2004 | Chappuis | A61B 17/1671 606/86 R |
| 2004/0143268 | A1* | 7/2004 | Falahee | A61B 17/1757 606/247 |
| 2005/0043797 | A1* | 2/2005 | Lee | A61B 17/686 623/17.11 |
| 2005/0177240 | A1* | 8/2005 | Blain | 623/17.15 |
| 2005/0197660 | A1* | 9/2005 | Haid | A61B 17/7064 606/86 A |
| 2006/0004367 | A1* | 1/2006 | Alamin | A61B 17/842 606/74 |
| 2006/0190081 | A1* | 8/2006 | Kraus | A61B 17/7064 623/17.11 |
| 2006/0235403 | A1* | 10/2006 | Blain | 606/69 |
| 2007/0179617 | A1* | 8/2007 | Brown | A61B 17/562 623/17.13 |
| 2009/0024166 | A1* | 1/2009 | Carl | A61F 2/4405 606/247 |

OTHER PUBLICATIONS

International Preliminary Report on Patentability for International App. No. PCT/US2009/040559, dated Oct. 19, 2010.

* cited by examiner

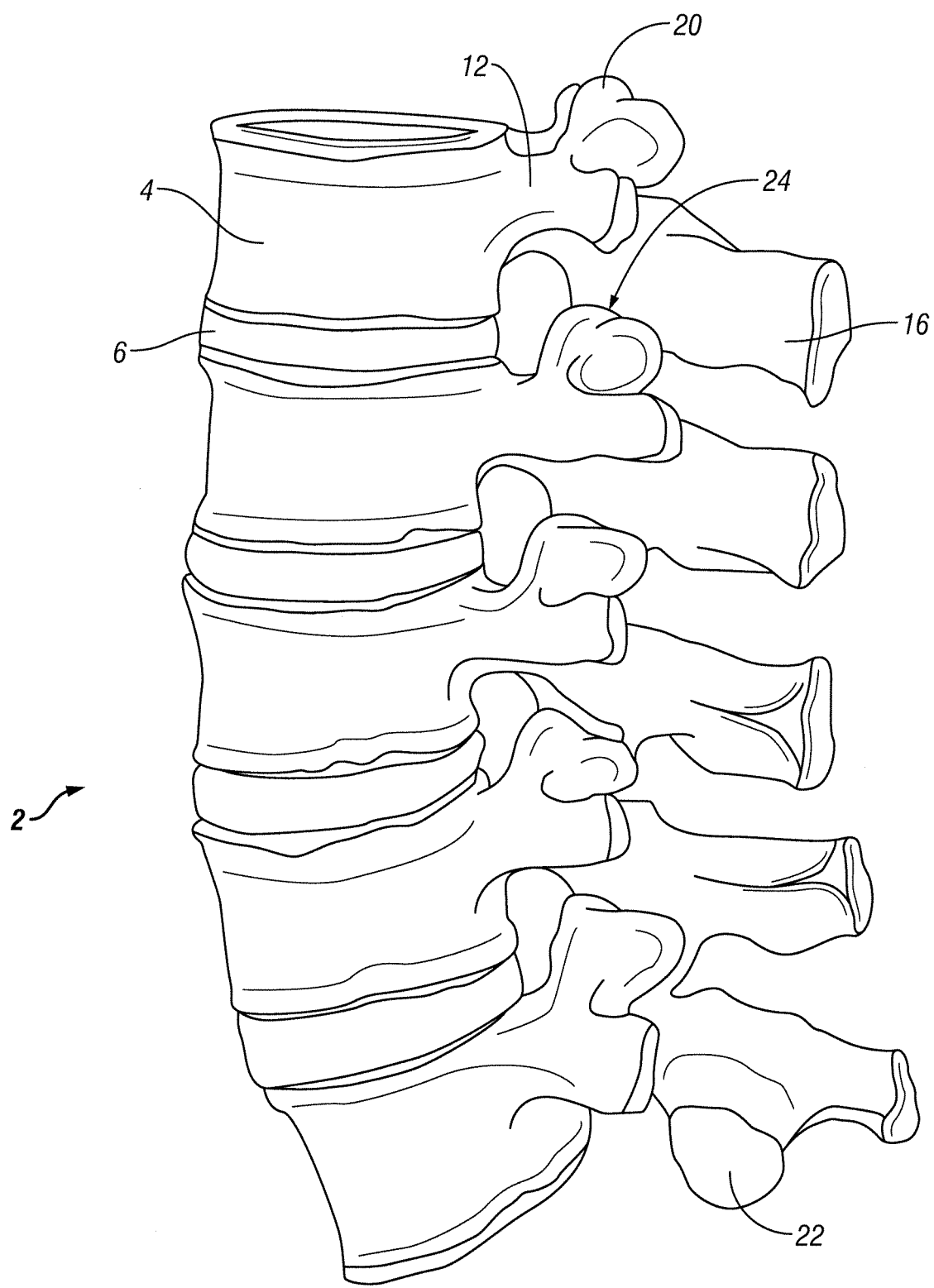
F I G . 1

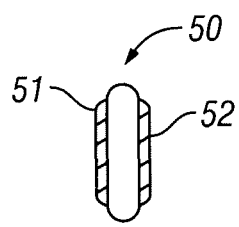
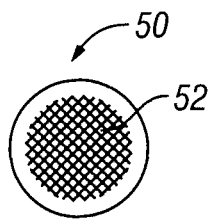
FIG. 14A	FIG. 14B
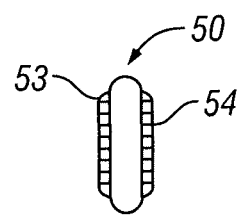
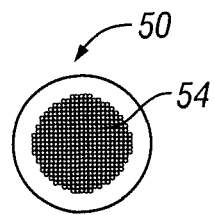
FIG. 15A	FIG. 15B
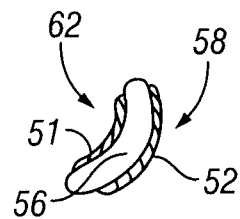
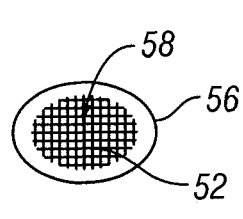
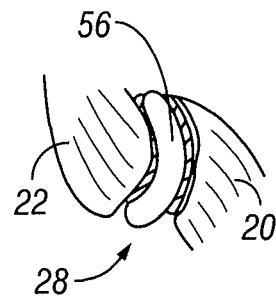
FIG. 16A	FIG. 16B	FIG. 17
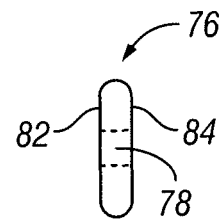
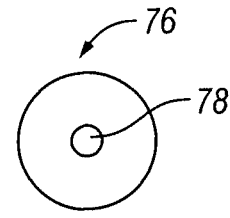
FIG. 18A	FIG. 18B
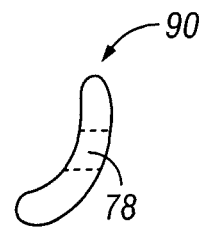
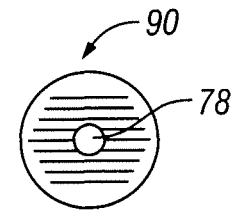
FIG. 19A	FIG. 19B

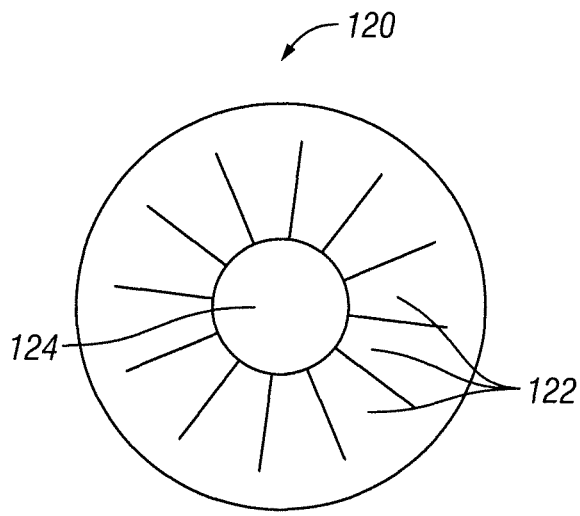
FIG. 29A  FIG. 29B
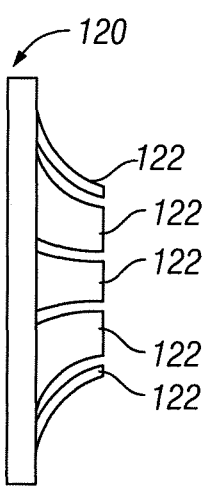 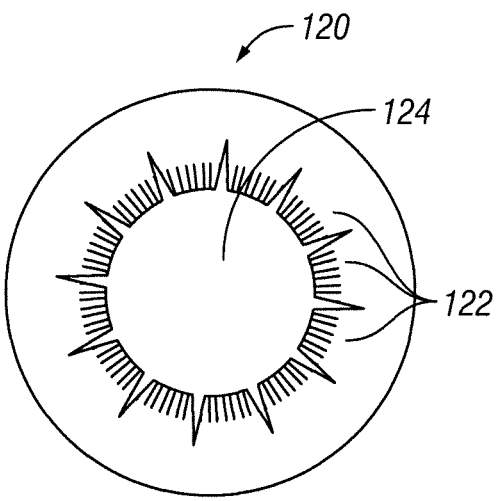
FIG. 30A  FIG. 30B

IMPLANT AND METHOD FOR FACET IMMOBILIZATION

CROSS-REFERENCE TO RELATED APPLICATIONS

This application is a continuation-in-part of U.S Ser. No. 10/865,073 filed Jun. 10, 2004 (now U.S. Pat. No. 7,846,183).

FIELD OF THE INVENTION

The present invention relates to an implant and method for immobilizing a vertebral facet joint.

BACKGROUND INFORMATION

Traumatic, inflammatory, and degenerative disorders of the spine can lead to severe pain and loss of mobility. For example, back and spinal musculoskeletal impairments are significant causes of lost work productivity in the United States. Pain as a result of some type of spinal impairment may have its source in a variety of pathologies or clinical conditions.

As shown in FIG. 1, the vertebral column 2 of the spine includes a series of alternating vertebrae 4 and fibrous discs 6 that provide axial support and movement to the upper portions of the body. The vertebral column 2 typically includes thirty-three vertebrae 4, with seven cervical (C1-C7), twelve thoracic (T1-T12), five lumbar (L1-15), five fused sacral (S1-S5) and four fused coccygeal vertebrae.

FIGS. 2A and 2B depict a typical thoracic vertebra. Each vertebra includes an anterior body 8 with a posterior arch 10. The posterior arch 10 has two pedicles 12 and two laminae 14 that join posteriorly to form a spinous process 16. Projecting from each side of the posterior arch 10 is a transverse 18, superior 20 and inferior articular process 22. The facets 24, 26 of the superior 20 and inferior articular processes 22 form facet joints 28 where they align with the articular processes of the adjacent vertebrae, as shown in FIGS. 3A and 3B. The facet joints are true synovial joints, with cartilaginous surfaces and a joint capsule.

The orientation of the facet joints vary, depending on the level of the vertebral column. FIGS. 4A to 6B depict the orientations of the facet joints at different levels of the vertebral column. In the C1 and C2 vertebrae (not shown), the facet joints are substantially parallel to the transverse plane.

In the C3 to C7 vertebrae shown in FIGS. 4A and 4B, the facets are oriented at an approximately 45-degree angle to the transverse plane 30 and are substantially parallel to the frontal plane 32. This orientation allows the facet joints of the cervical vertebrae to flex, extend, laterally flex, and rotate. The 45-degree angle orientation with respect to the transverse plane 30 allows the facet joints of the cervical spine to guide the movement of the cervical vertebrae without limiting such movement.

FIGS. 5A and 5B depict the thoracic vertebrae, which include facets oriented at an approximately 60-degree angle to the transverse plane 30 and an approximately 20-degree angle to the frontal plane 32. This orientation is capable of allowing lateral flexion and rotation, but only limited flexion and extension.

FIGS. 6A and 6B illustrate the lumbar region, where the facet joints are oriented at approximately 90-degree angles to the transverse plane 30 and an approximately 45-degree angle to the frontal plane 32. The lumbar vertebrae allow flexion, extension and lateral flexion of the lumbar region, but little, if any, rotation because of the 90-degree orientation of the facet joints in the transverse plane. The actual range of motion along the vertebral column can vary considerably with each individual vertebra.

In addition to guiding movement of the vertebrae, the facet joints also contribute to the load-bearing ability of the vertebral column. For example, facet joints can bear up to 30% of the load on the spine in some positions of the vertebral column as described, e.g., in King et al., Mechanism of Spinal Injury Due to Caudocephalad Acceleration, Orthop. Clin. North Am., 6:19 (1975). The facet joints may also play a role in resisting shear stresses between the vertebrae. Over time, these forces acting on the facet joints can cause degeneration and arthritis.

One source of back and spine pain is related to degeneration of the facets of the spine or facet arthritis. Bony contact or grinding of degenerated facet joint surfaces between two vertebrae may play a role in some pain syndromes. Such degenerative problems with the facet joints are often treated by fusing the two adjacent vertebrae together. By performing this surgical procedure, the relative motion between the two adjacent vertebrae is effectively stopped. This fusion procedure significantly reduces relative motion of the facets between the adjacent vertebrae. However, the facets between fused vertebrae may still exhibit some relative motion as the vertebral column is subjected to overall movement and various stresses. Such motion can lead to further problems, such as pain, arising from the degenerative facet joint.

Often, the facet joints between fused vertebrae are not treated as part of the fusion procedure. In certain procedures, the facets may simply be screwed together. However, because there is cartilage in the facet joints, the joints may not fuse and can still be a source of further discomfort.

Accordingly, there is a need to address the clinical concerns raised by degenerative facet joints, and to immobilize such facet joints when adjacent vertebrae are fused together.

SUMMARY OF THE INVENTION

Various implants have been proposed for addressing facet degeneration by restoring motion, and often require bony resection to be placed within the spine. Alternatively, facet joints are often left untouched when adjacent vertebrae are fused together, which substantially reduces motion within the facet joints between the vertebrae. However, even slight motion within the degenerated facet joints can lead to further discomfort and pain.

Embodiments of the present invention provide a method and device for immobilizing a facet joint. The method and device allow maintenance of the relative spacing between the facets within the facet joint, while allowing each of the adjacent articular surfaces of the facet joint to fuse to an implant provided between the facets. Such immobilization of the facet joint can alleviate the bone on bone contact that is common in degenerative facet joints and which may be a source of pain or discomfort even when the adjacent vertebrae are fused together.

In one aspect, embodiments of the invention provide a device for inhibiting movement at a facet joint which includes an implant. The faces of the implant are shaped such that they can be secured to the adjacent articular surfaces of the facet joint. The implant is dimensioned to fit substantially within the joint capsule of the facet joint. For example, the implant may have an average diameter that is between about 5 mm and about 25 mm, or between about 10 mm and about 20 mm.

The implant can be formed using a polymer, including but not limited to polyetheretherketone (PEEK), polyetherketoneketone (PEKK), or polyethylene; a ceramic including but not limited to zirconia, alumina, or silicon nitride; or a metal including but not limited to titanium, a titanium alloy, cobalt chromium, or a stainless steel. The implant can also be formed using other metals or metal alloys, an allograft, an autograft, or a combination of two or more of the above materials. The faces of the implant can be roughened or porous to improve bonding, friction, adherence, and/or osteoincorporation with the articular surfaces. For example, the implant can be made partially or entirely from a partially-sintered powdered metal.

The implant preferably has a thickness that is approximately the same as the normal anatomic spacing between the facets of the facet joint or slightly larger. For example, the thickness of the implant may be between about 0.5 mm and about 3 mm, or between about 1 mm and about 2 mm.

The implant may be configured to be bonded to the articular surfaces of the facets using an adhesive or a sealant. Alternatively, the device may include an anchoring arrangement configured to maintain the implant in a fixed position relative to the adjacent articular surfaces of the facet joint. The anchoring arrangement can also provide a compressive force between the implant and the articular surfaces to better immobilize the facet joint. For example, the anchoring arrangement is preferably configured to pass through holes formed in the implant and articular processes associated with the facet joint. The anchoring arrangement is preferably a rigid fastener such as a threaded retainer, e.g., a threaded bolt, or a rod or cylinder which includes a flange, a retainer ring or disc, or a threaded nut provided at one or both ends. The anchoring arrangement can also be curved or bent along its primary axis.

In a further aspect, a method of treating vertebral dysfunction by immobilizing a facet joint is provided, in which an incision is made above the facet joint and the facet joint capsule is opened. Some or all of the cartilage within the facet joint is removed, and the articular surfaces may optionally be roughened. An implant is then placed within the facet joint between the articular surfaces and secured therein. In certain embodiments, the implant is secured using an adhesive or a sealant.

In further embodiments, an anchoring arrangement is provided to secure the implant to the articular processes and immobilize the facet joint. For example, a hole can be formed through the implant and the articular processes of the facet joint. A retaining member, which preferably has the shape of a rod or cylinder, is then inserted through the holes, and one or more fasteners are provided at the ends of the retaining member to secure the articular processes and implant together. The fasteners can include, for example, a threaded nut, a retainer ring with a set screw, a disc with a friction fit, or a flange.

After the facet joint is immobilized, the incision is closed and allowed to heal.

BRIEF DESCRIPTION OF THE DRAWINGS

Further objects, features and advantages of the invention will become apparent from the following detailed description taken in conjunction with the accompanying figures showing illustrative embodiments, results and/or features of the present invention, in which:

FIG. 1 is a lateral elevational view of a portion of the vertebral column;

FIGS. 14A and 14B are schematic views of a facet joint implant having a disc shape with roughened surfaces;

FIGS. 15A and 15B are schematic views of a facet joint implant having a disc shape with porous surfaces;

FIGS. 16A and 16B are schematic views of a facet joint implant having a bent disc shape with roughened surfaces;

FIG. 17 is a schematic view of the implant of FIG. 16A implanted in a facet joint;

FIGS. 18A and 18B are schematic views of a facet joint implant which includes a centrally located hole;

FIGS. 19A and 19B are schematic views of a facet joint implant having a curved disc shape which includes a centrally located hole;

FIGS. 29A and 29B are friction fit retaining rings shown in a relaxed state;

FIGS. 30A and 30B depict the retaining rings of FIGS. 29A and 29B in an expanded state.

Figure 2A:
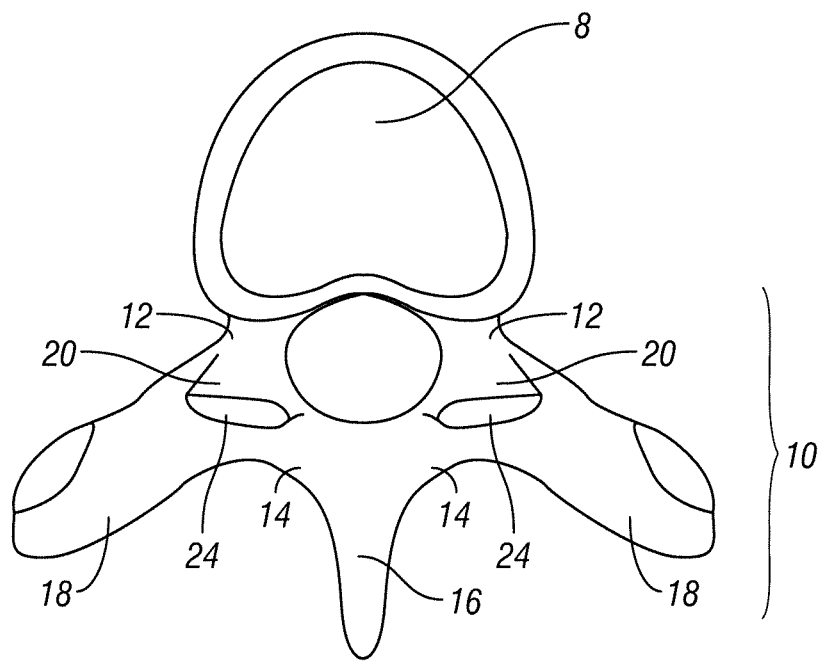
FIGS. 2A and 2B are schematic superior and side views, respectively, of an isolated thoracic vertebra.
Figure 2B:
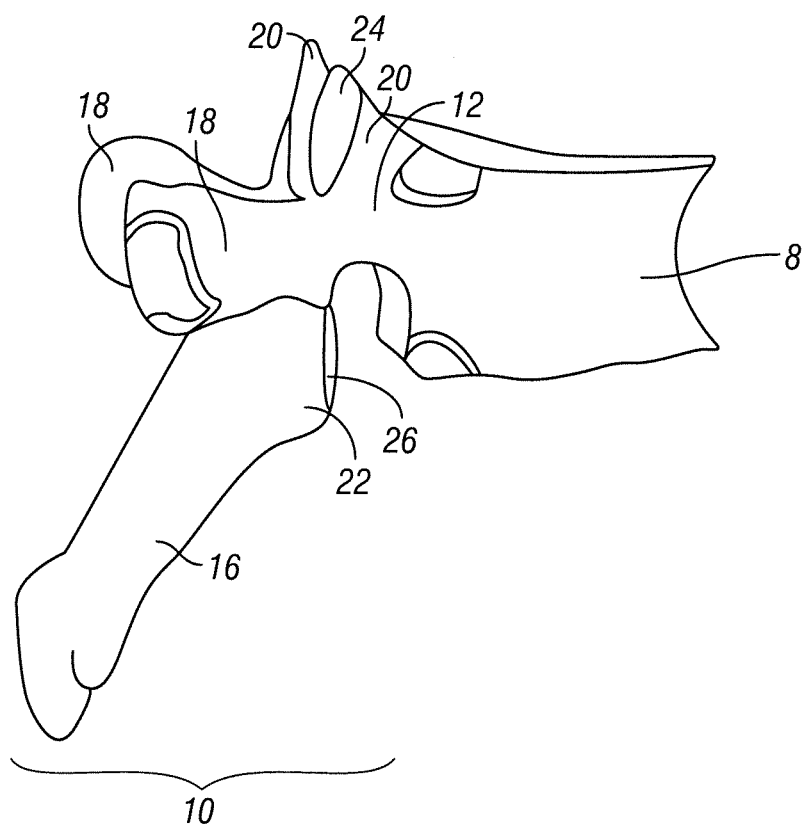
Figure 3A:
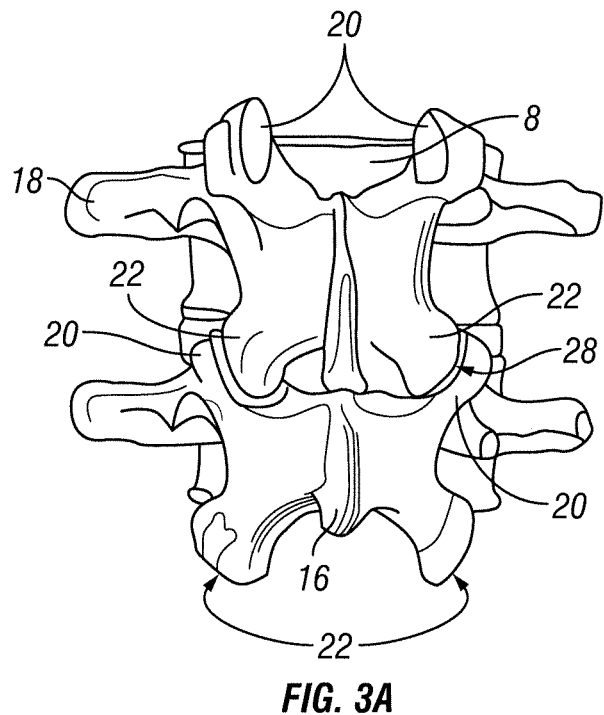
FIGS. 3A and 3B are schematic posterior and posterior-oblique elevational views, respectively, of a portion of the vertebral column.
Figure 3B:
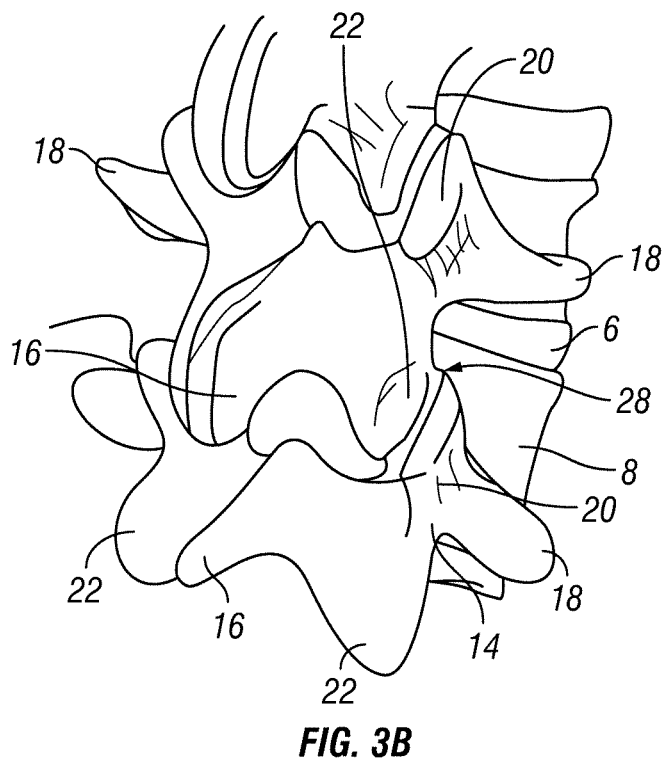
Figure 4A:
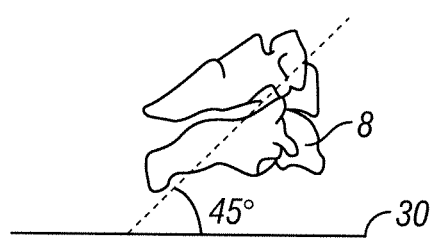
FIGS. 4A and 4B are schematic side and superior views, respectively, of a facet joint in the cervical vertebrae.
Figure 4B:
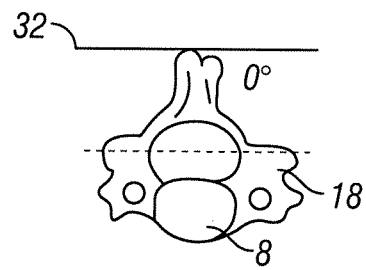
Figure 5A:
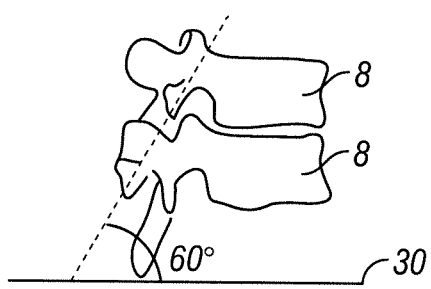
FIGS. 5A and 5B are schematic side and superior views, respectively, of a facet joint in the thoracic vertebrae.
Figure 5B:
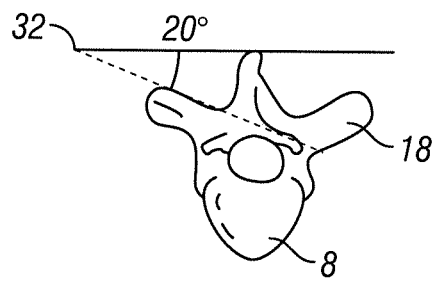
Figure 6A:
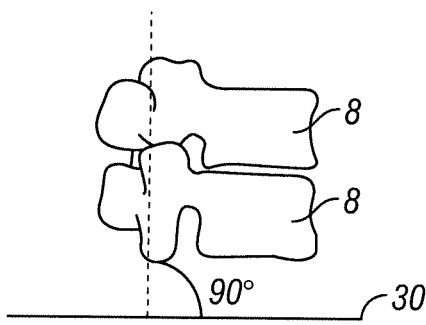
FIGS. 6A and 6B are schematic side and superior views, respectively, of a facet joint in the lumbar vertebrae.
Figure 6B:
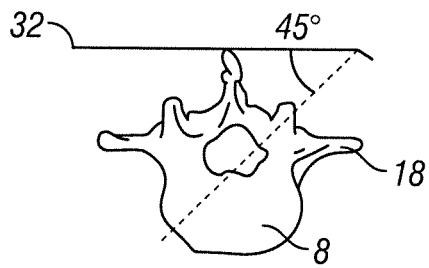

Throughout the drawings, the same reference numerals and characters, unless otherwise stated, are used to denote like features, elements, components, or portions of the illustrated embodiments. Moreover, while the present invention will now be described in detail with reference to the figures, it is done so in connection with the illustrative embodiments and is not limited by the particular embodiments illustrated in the figures.

DETAILED DESCRIPTION OF EMBODIMENTS OF THE INVENTION

Figure 7A:
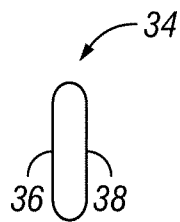
FIGS. 7A and 7B are schematic views of a facet joint implant having a circular disc shape.
Figure 7B:
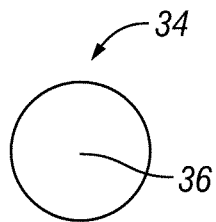

In one aspect, embodiments of the present invention provide a device for immobilizing a facet joint, and which can further maintain a spacing between the two facets of the immobilized facet joint. As shown in FIGS. 7A and 7B, the device includes an implant 34 with two faces: a first face 36 adapted to contact the articular surface of one facet of the facet joint and a second face 38 adapted to contact the articular surface of the other facet.

The implant can be formed from any of a variety of materials known in the art, including but not limited to a polymer such as polyetheretherketone (PEEK), polyetherketoneketone (PEKK), or polyethylene. Alternatively, the implant can be formed from a ceramic such as zirconia, alumina, or silicon nitride. The implant may also be formed from a metal including, but not limited to, titanium, a titanium alloy, cobalt chromium, or a stainless steel. The implant can also be formed from a wafer of allograft material or autograft material, which can promote growth of bone tissue from the facets into the implant. The implant can also be formed from a combination of two or more of the materials cited herein.

Figure 8:
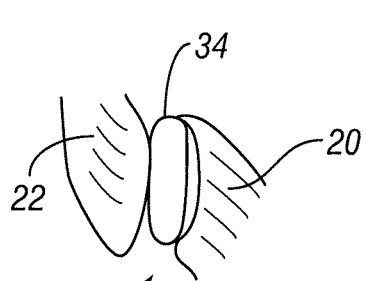
FIG. 8 is a schematic view of the implant of FIG. 7A implanted in a facet joint.
Figure 9A:
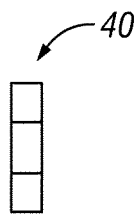
FIGS. 9A and 9B are schematic views of a facet joint implant having an octagonal disc shape.
Figure 9B:
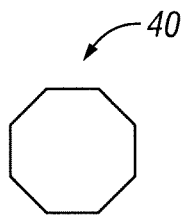

In one embodiment, the implant 34 has a generally circular profile and is sized to fit substantially within the joint capsule of the facet joint 28. FIG. 8 illustrates the implant 34 of FIGS. 7A and 7B positioned in a facet joint to be immobilized. In other embodiments, the implant can have any of a variety of profiles, including but not limited to square, rectangle, oval, star, polygon or a combination or variation thereof. For example, an octagonal implant 40 is shown in FIGS. 9A and 9B. The shape of a particular implant can be selected based on radiographic or other visualization of the articular processes and/or the joint capsule. The shape of the implant is preferably selected so the two faces contact a substantial portion of the articular surfaces of the two facets of the facet joint.

In one embodiment, the implant has a diameter between about 4 mm and about 30 mm. In another embodiment, the implant has a diameter between about 5 mm and about 25 mm. In still another embodiment, the implant has a diameter between about 10 mm and about 20 mm. If the implant is not circular in shape, the diameter can refer to the longest dimension measured across one of the two faces thereof. The diameter of a particular implant can be selected based on the size of the articular surfaces in the facet joint to be immobilized, which varies with location in a particular vertebral column. Preferably, the diameter of the implant should not be so large that the implant protrudes significantly beyond the edges of the articular surfaces, and is large enough such that the faces of the implant contact a substantial portion of the articular surfaces. Further, the implant should not protrude past the periphery of the facet joint closest to the vertebral column, as such protrusion may interfere with a disc or the spinal cord.

The implant preferably has a thickness approximately the same as the anatomic spacing between two facets of the facet joint to be immobilized. For example, the implant generally has a thickness between about 0.5 mm and about 3.0 mm. In certain embodiments, the implant has a thickness between about 1 mm and about 2 mm. In further embodiments, the implant has a thickness between about 0.5 mm and about 1.5 mm. The thickness of the implant may also be slightly larger than the anatomic spacing between two facets of the facet joint. A thicker implant can improve contact between the implant faces and the articular surfaces when the implant 34 is placed between the facets 20, 222 as shown, for example, in FIG. 8.

Figure 10A:
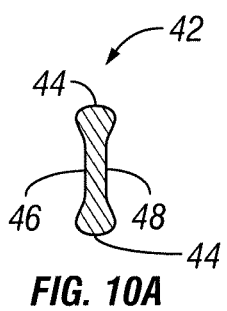
FIGS. 10A and 10B are schematic views of a facet joint implant having a biconcave disc shape.
Figure 10B:
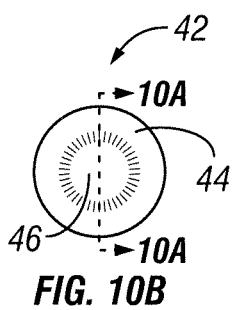
Figure 11A:
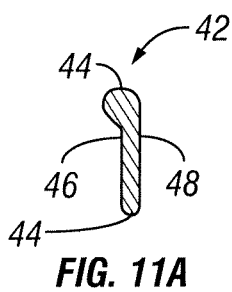
FIGS. 11A and 11B are schematic views of a facet joint implant having a single-face variable thickness disc shape.
Figure 11B:
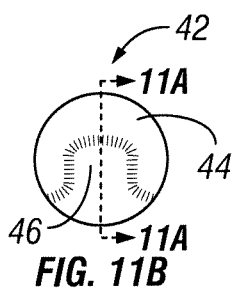

The implant can be configured to provide an improved fit with the articular process and/or joint capsule. In certain embodiments, the thickness of a particular implant is non-uniform. For example, in FIGS. 10A and 10B, the thickness of the implant 42 is increased around the entire outer edge 44 along both faces 46, 48. In FIGS. 11A and 11B, only a portion of the edge 44 on one face 46 of the implant 42 has a thickness that is greater than the thickness of a central region, and, optionally, also thicker than the typical anatomic spacing between two facets of a facet joint. Such variations in thickness of the implant may also resist lateral displacement of the implant out of the facet joint.

Figure 13:
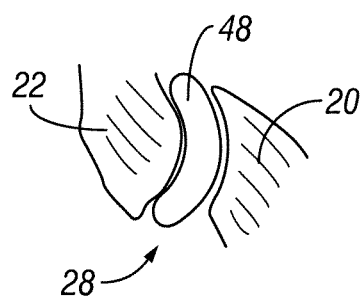
FIG. 13 is a schematic view of the implant of FIG. 12A implanted in a facet joint.
Figure 12A:
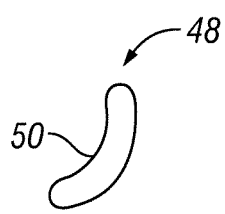
FIGS. 12A and 12B are schematic views of a facet joint implant having a curved disc shape.
Figure 12B:
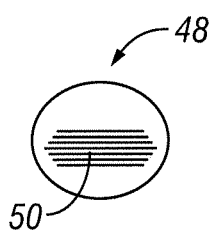

In certain embodiments, the implant may also be shaped to better conform to the shape of the articular surfaces of a facet joint. For example, the implant 49 shown in FIGS. 12A and 12B has a bend, angle or curve 50 to more closely match the natural shape of an articular facet. FIG. 13 depicts the implant 49 shown in FIGS. 12A and 12B positioned in a facet joint. The implant may be rigid with a preformed bend. Alternatively, the implant may be sufficiently malleable that it will conform to some degree to the specific configuration of the adjacent facet surfaces when placed between them.

In embodiments of the present invention, the facet joint capsule is incised and at least a portion of the cartilage is removed from the joint space between the facets before the implant is placed therein. Preferably, enough of the cartilage in the facet joint is removed such that all or a substantial portion of the articular surfaces of the facets are exposed. One or both of the adjacent articular surfaces can be roughened to improve contact with the implant and reduce slippage between the implant faces and the articular surfaces of the facets.

Preferably, at least a portion of each face of the implant is porous and/or roughened. In one embodiment, shown in FIGS. 14A and 14B, at least a portion of the surfaces 51, 52 of the implant 50 are roughened. Such roughening can improve adhesion and reduce slippage between the surfaces 51, 52 and the articular faces of the facet joint.

In a further embodiment, at least a portion of the surfaces 53, 54 of the implant 50 are porous as shown in FIGS. 15A and 15B. The porous surfaces 53, 54 can be created in any of a variety of conventional techniques, such as by applying sintered beads or spraying plasma onto the implant surface. Alternatively, the implant 50 can be made partially or entirely from a porous material such as a partially-sintered powder metal form. For example, porous surfaces 53, 54 can allow bone to grow into or attach to the surfaces 53, 54 of the implant 50, thus securing the implant 50 to the bone in the adjacent facets.

A curved implant 56 is shown in FIGS. 16A and 16B. The implant has a convex face 58 with a roughened surface 52, and a concave face 62 with a roughened face 51. The implant 56 can be placed in the facet joint 28 between facets 20, 22, as shown in FIG. 17. The implant 56 is shaped to provide good contact with the articular surfaces of the facets 20, 22. The roughened faces 51, 52 of the implant 56 can promote friction and/or adhesion between the articular surfaces and the implant 56, promoting immobilization of the facet joint 28. The roughened faces 51, 52 of the implant 56 (or, alternatively, porous faces of the implant if provided) may also promote growth of bone from the articular surfaces of the facets 20, 22 into the implant to fuse the facet joint. As shown in FIG. 17, the spacing between the facets 20, 22, can be substantially the same when the implant 56 is inserted as the spacing before fusion of the joint 28 using the implant 56.

In certain embodiments of the invention, the implant is maintained between the two facets of the facet joint by taking advantage of the joint capsule and/or other body tissue surrounding the facet joint to limit the migration of the implant out of the facet joint. For example, the shape of the implant itself may be capable of resisting displacement of the implant from its position generally between the facet joint surfaces. A concave or biconcave configuration, such as that shown in FIGS. 10A and 10B, may resist displacement of the implant by providing an increased thickness at the periphery of the implant that requires a larger force and/or greater distraction of facet joint surfaces in order to cause displacement. Surface treatments or texturing of the implant can also be used to maintain the implant against the articular surfaces of the facet joint, as described herein. Further, a combination of disc configuration, surface texturing, and existing body tissue or structures can be used to maintain the position of the implant between the facets of the facet joint to be immobilized.

In one embodiment, an adhesive or sealant, such as a cyanoacrylate, polymethylmethacrylate, or another biocompatible adhesive, is used to bond the faces of the implant to the adjacent articular surfaces of the facet joint. Such bonding can promote fusion of the facet joint. In a further embodiment, bone growth facilitators, electrical current, or other conventional techniques may be used to accelerate osteoincorporation of textured or porous anchoring surfaces of the implant.

In further embodiments, the device further includes an anchoring arrangement configured to secure the implant in a fixed position relative to the adjacent facets. The anchoring arrangement preferably provides a compressive force between the implant and the facets to promote adhesion and/or osteoincorporation of the implant with the articular surfaces of the facets.

Figure 20:
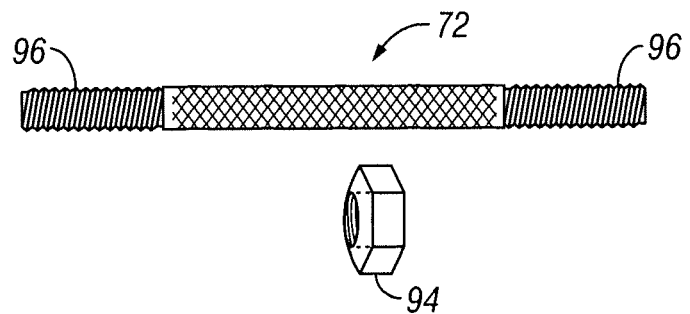
FIG. 20 depicts a retaining member which in the shape of a rod or cylinder with threaded ends adapted to accept threaded nuts.

In one embodiment of the invention, a hole 78 is provided through the implant 76 between opposite faces 82, 84, as shown in FIGS. 18A and 18B. Alternatively, the hole 78 can be provided through a curved implant 90, as shown in FIGS. 19A and 19B. The anchoring assembly includes a retaining member 72, which can have the shape of a rod or cylinder and is preferably made from a rigid material, as shown in FIG. 20. The anchoring assembly further includes two threaded nuts 94 which are configured to engage with threaded ends 96 of the retaining member 72.

Figure 21:
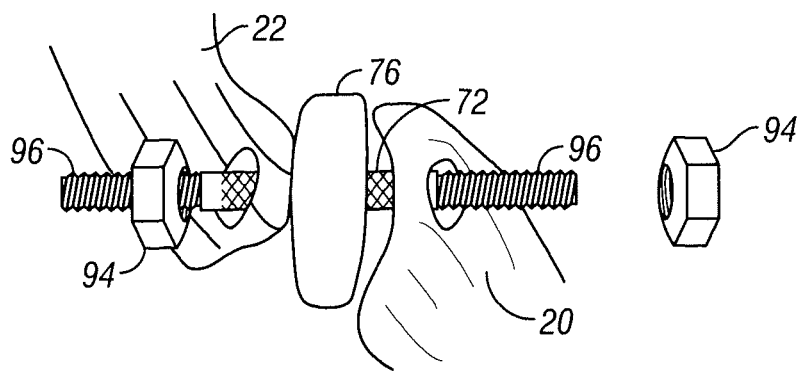
FIG. 21 depicts the retaining member of FIG. 20 which is used to affix the implant to the articular processes of a facet joint using threaded nuts.

A hole is formed through both articular processes 20, 22 of the facet joint to be immobilized or fused, as shown in FIG. 21. The implant 76 is placed between the facets and the retainer member 72 is inserted through the hole in each articular process 20, 22 and through the hole 78 in the implant 76, also shown in FIG. 20. Each nut 94 can then be threaded onto a threaded end 96 of the retaining member 72, and tightened to secure the articular processes 20, 22 to the implant 76, and to provide a compressive force between the facets and the implant 76. Such force can provide substantial immobilization of the facet joint and/or help promote osteoincorporation of the implant 76 with the articular surfaces of the facet joint. The threaded portion 96 is preferably made from titanium, a titanium alloy, cobalt chromium, a stainless steel, another metal alloy, or a combination of two or more such materials.

The diameter of the hole 78 in the implant 76 and the diameters of the holes in the articular processes 20, 22 are preferably at least slightly larger than the diameter of the retainer member 72. This allows the retainer member 72 to be easily inserted through the holes, and can also allow the implant 76 and the articular processes 20, 22 to move freely with respect to the retainer member 72 when the nuts 94 are tightened onto the threaded ends 96. This can assist in providing compressive forces between the faces of the implant 76 and the adjacent facet surfaces when the nuts 94 are tightened on the retainer member 72.

The hole 78 can be formed in the implant 76 before it is inserted into the facet joint. Alternatively, the hole 78 can be formed together with the holes through the articular processes 20, 22 after the implant 76 is placed in the facet joint. Such holes can be formed by drilling, by using a punch, or by other conventional techniques suitable for creating a hole in the bone and implant materials.

The cross-sectional shape of the retaining member 72 can be selected from a variety of shapes, including but not limited to circles, ovals, squares, rectangles, other polygons, or other shapes. A circular shape is preferred to better conform to the threaded ends 96 and to provide a close fit with the drilled or punched holes in the articular processes 20, 22. The retaining member 72 generally has a diameter between about 0.25 mm and about 2 mm, or between about 0.5 mm and about 1.25 mm, or preferably between about 0.75 mm and about 1.25 mm. The diameter of the retaining member 72 may optionally vary along its length. The diameter of a particular retaining member 72 may be selected based on the facet joint being immobilized. For example, a larger diameter can be used for immobilizing facet joints in the lower vertebrae (e.g., lumbar vertebrae) which tend to have larger facets. Similarly, a smaller diameter can be used for immobilizing facet joints in the upper vertebrae (e.g., cervical vertebrae) which tend to have smaller facets.

The retaining member 72 has a length that is generally between about 5 mm and about 60 mm, or between about 10 mm and about 40 mm. The retaining member 72 can have a length of about 20 mm to about 30 mm. The length of a particular retaining member 72 may be selected based on the facet joint being immobilized. For example, a longer retaining member 72 can be used for immobilizing facet joints in the lower vertebrae (e.g., lumbar vertebrae) which tend to have thicker articular processes 20, 22. Similarly, a shorter retaining member 72 can be used for immobilizing facet joints in the upper vertebrae (e.g., cervical vertebrae) which tend to have thinner or smaller articular processes 20, 22. In general, it is preferable that the ends of the retaining member 72 do not protrude too far from the surfaces of the articular processes 20, 22 when inserted into the holes therethrough, but the retaining member 72 should be long enough to allow engagement of the nuts 94 onto the threaded ends 96.

Figure 22:
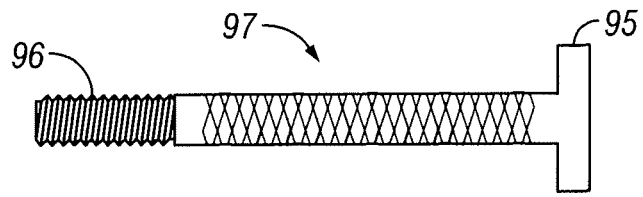
FIG. 22 depicts a retaining member which in the shape of a rod or cylinder with one threaded end adapted to accept a threaded nut and a flange provided at the opposite end.

In a further embodiment, shown in FIG. 22, the retaining member 97 is provided with a flange 95 at or near one end, and a single threaded end 96 at the opposite end. For example, the retaining member 97 can be a bolt having suitable dimensions and made from a suitable material. The threaded end 96 can be inserted through holes in the implant 76 and articular processes 20, 22, and a single nut 94 can be threaded onto the threaded end 96 to immobilize the facet joint and optionally provide a compressive force across the joint. The flange 95 is preferably larger in diameter than the hole diameters, such that it can engage one of the articular processes 20, 22. The flange 96 can be provided in any of a variety of shapes. For example, the side of the flange 95 closest to the threaded end 96 can be shaped to approximately conform to the outer surface of the articular process around the hole therethrough, to provide better contact and a more uniform force between the flange 95 and the articular process.

Figure 23A:
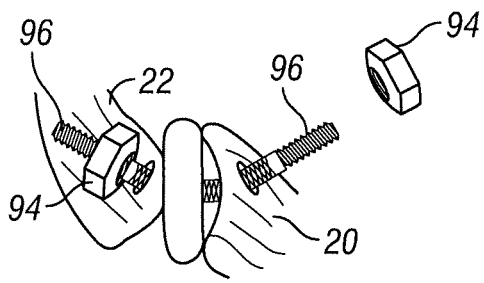
FIG. 23A depicts a curved retaining member which is used to affix the implant to the articular processes of a facet joint together with threaded nuts.

In another embodiment, the retaining member 72 of the anchoring assembly has a bend or a curve along the main axis, as shown in FIG. 23A. The bend or curve can provide a better orientation for the nuts 94 with respect to the articular processes 20, 22 for certain facet joints. For example, a curved retaining member 72 may allow the nuts to be positioned approximately flush with an outer surface of the articular processes 20, 22 when the nuts 94 are threaded onto the threaded ends 96.

Figure 23B:
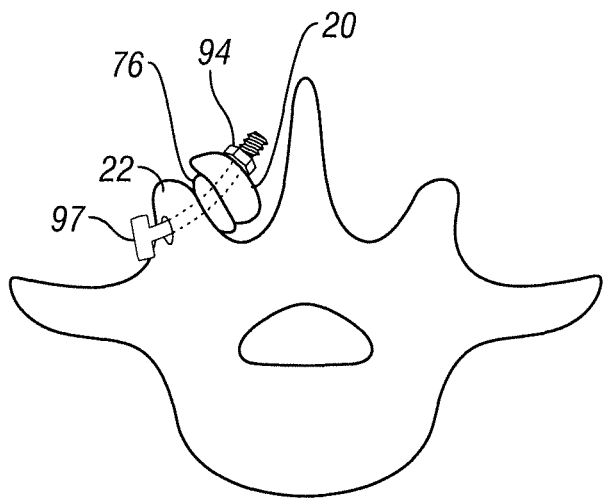
FIG. 23B depicts a retaining member which is a curved bolt that is used to affix the implant to the articular processes of a facet joint together with a threaded nut.

In a further embodiment, shown in FIG. 23B, a retaining member 97 such as that shown in FIG. 22, which may be a bolt or the like, can be provided with a bend or curve such that it passes through holes in the articular processes 20, 22, and optionally through an implant 76, if such implant is provided in the facet joint. A nut 94 is threaded onto the distal end of the fastener 97 to secure the articular processes 20, 22 of the facet joint together, as shown in FIG. 23B. Such a curve or bend can be provided in any of the various exemplary retaining member configurations described herein.

Figure 24:
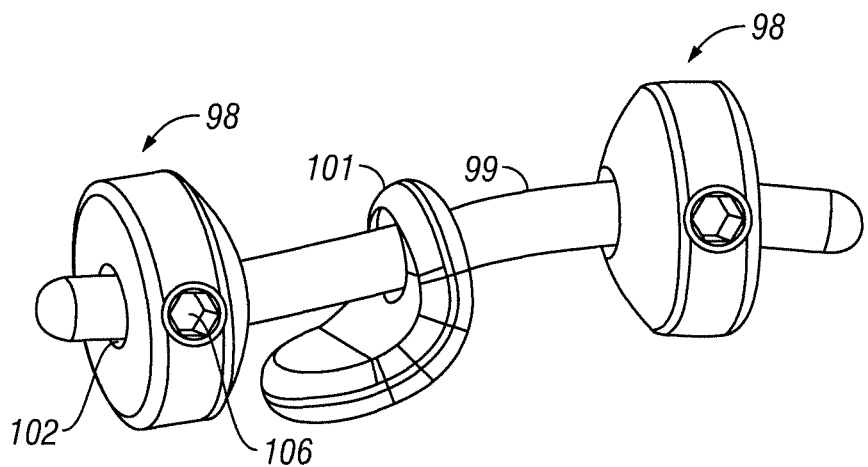
FIG. 24 depicts a retaining member in the shape of a rod or cylinder which is adapted to accept two set-screw retaining rings.
Figure 25A:
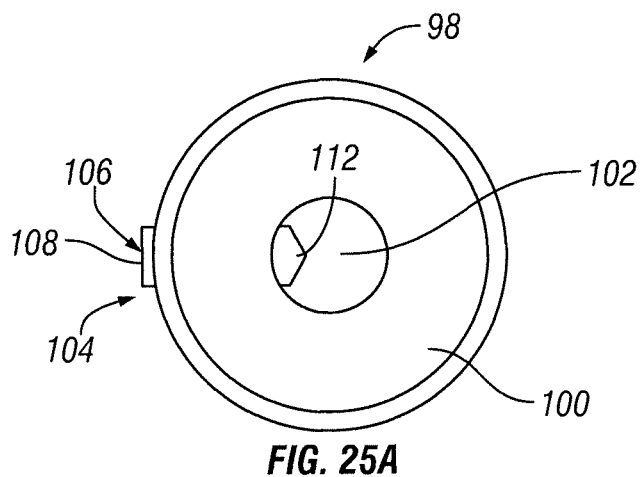
FIGS. 25A and 25B are elevational and cross-sectional views, respectively, of the set-screw retaining rings shown in FIG. 24.
Figure 25B:
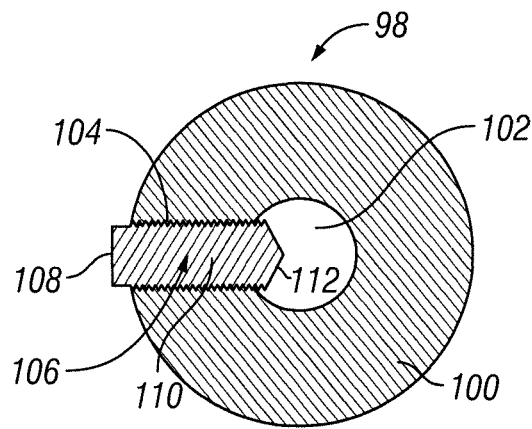

In another embodiment, shown in FIG. 24, the anchoring arrangement includes a retaining member 99 which can be secured to the articular process with retaining rings 98 instead of with threaded nuts. As depicted in FIGS. 25A and 25B, the retaining rings 98 include a ring 100 with a central lumen 102 and a locking element to facilitate locking the ring 100 to the retaining member 99. The central lumen 102 is adapted to accept insertion of the retaining member 99 therethrough. The retaining member 99 also passes through a hole in the implant 101 when placed in the facet joint, similar to the configuration shown in FIG. 21. The illustrated locking element includes a side lumen 104 which is threaded and configured to accept a rotatable screw 106 (e.g., a "set screw") with a proximal end 108, a threaded body 110 and a distal end 112. The threaded body 110 is complementary to the threads of the side lumen 104 so that when the screw 106 is rotated at its proximal end 108, the distal end 112 of the screw 106 moves further into the central lumen 102 and is capable of applying increasing force to the retaining member 99 inserted through the central lumen 102.

Figure 26:
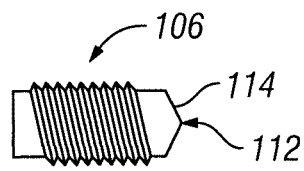
FIGS. 26 through 28 are elevational views of various embodiments of the screw in the set-screw retaining rings.
Figure 27:
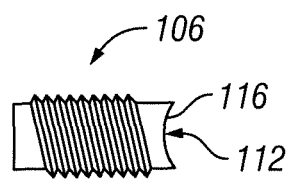
Figure 28:
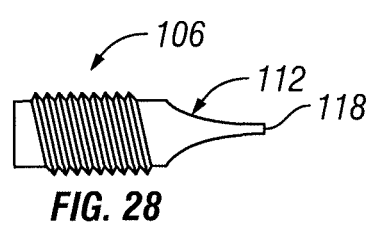

In one embodiment, the force on the retaining member 99 is capable of creating a friction fit or a mechanical fit to resist movement between the retaining member 99 and the retaining ring 98, thereby securing the retaining member 99 to the articular process 20 or 22. As shown in FIGS. 26-28, the distal end 112 of the screw 106 can be configured to engage the retaining member 99 using any of a variety designs, including but no limited to a blunt tip 114, a curved tip 116, or a piercing tip 118.

In another embodiment, depicted in FIGS. 29A and 29B, the retaining member 99 is securable to the articular process 20 or 22 with a retaining disc 120 have radially inward biased projections 122 defining a central lumen 124. The central lumen has a cross-sectional diameter that is smaller than that of the retaining member 99 but is capable of enlargement when the inward projections 122 are bent away, as shown in FIGS. 30A and 30B. The inward projections 122 apply increasing force to the retaining member 99 within the central lumen 124 as the projections 122 are bent, thereby creating a friction fit. The outer perimeter of the retaining disc 120 can have a shape that is non-circular. For example, the shape of the retaining disc 120 can be oval or ovoid, rectangular, polygonal, or any other shape surrounding a central lumen.

In still further embodiments, the retaining member is configured to accept a retaining ring 98 or a retaining disc 120 at or near one end, and has a single threaded end 96 at the opposite end. The retaining member can be inserted through holes in the implant and articular processes 20, 22, and the retaining ring 98 or retaining disc 120 can be fastened at or near the one end of the retaining member as described herein. A single nut 94 can then be threaded onto the threaded end 96 to immobilize the facet joint and more easily provide a compressive force across the joint.

Figure 31:
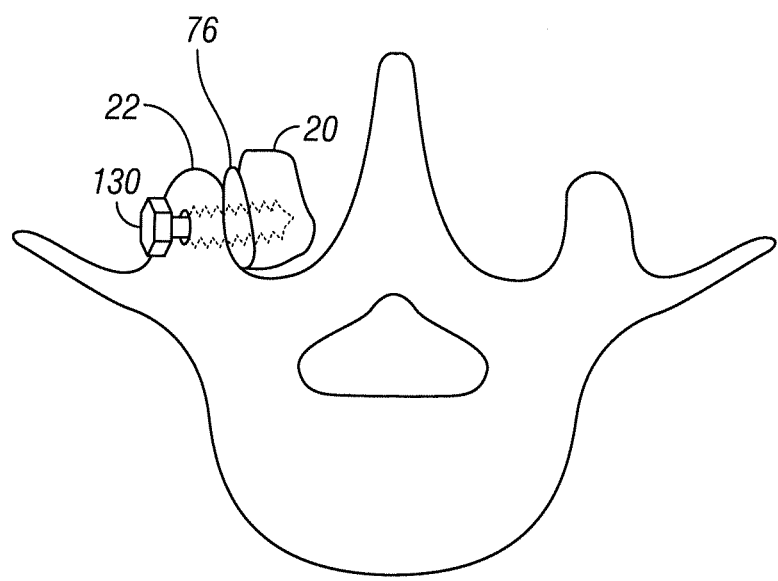
FIG. 31 depicts a retaining member which is a bone screw that is used to affix the implant to the articular processes of a facet joint.

In a still further embodiment, shown in FIG. 31, the retaining member is a bone screw 130 or the like. The bone screw 130 is placed from the medial side of the facet joint to the lateral side thereof, such that it passes through the articular processes 20, 22, and through an implant 76 provided in the facet joint. A small pilot hole can be formed in the articular processes 20, 22 and/or in the implant 76 prior to the insertion of the bone screw 130. Alternatively, the bone screw 130 can be screwed directly through the bone and the implant 76.

In a further aspect, embodiments of the invention provide a method for immobilizing a facet joint. First, a midline skin incision is made over the desired vertebrae, or a paraspinous skin incision is made over the particular facet joint to be immobilized. The facet joint capsule is incised and at least a portion of the cartilage is removed from the joint space between the facets. Preferably, substantially all of the cartilage is removed from the joint space to expose all or a substantial portion of the articular surfaces of the facets. One or both of the adjacent articular surfaces can be roughened to improve contact with an implant and reduce slippage between the implant faces and the articular surfaces of the facets. Such roughening may also promote osteoincorporation of the implant with the articular surfaces.

An implant is provided as described herein that is configured to be positioned within the facet joint. Preferably, at least a portion of each face of the implant is porous and/or roughened. The implant 56 is then inserted into the facet joint 28 between the articular surfaces 20, 22 as shown in FIG. 17. The implant 56 is preferably shaped such that it fits substantially within the facet joint 28 and conforms to the shape of the facet surfaces.

In one embodiment, the implant is bonded to at least a portion of the articular surfaces using an adhesive or sealant, such as a cyanoacrylate, polymethylmethacrylate, or another biocompatible adhesive. Preferably, the thickness of the implant is slightly larger than the natural distance between the opposing articular surfaces. A thicker implant can provide some compressive force between the implant and the articular surfaces, which can help to maintain the implant in a desired position and result in a more secure bond.

In further embodiments, a hole is then formed through the articular surfaces 20, 22 as shown in FIG. 21. A hole can also be formed in the implant 76 at this time, or the implant 76 may be provided with a hole therethrough before it is inserted into the facet joint. A drill, a punch, or any other conventional apparatus or technique can be used to form the holes.

An anchoring arrangement is then used to secure the implant in a fixed position relative to the adjacent facets. The anchoring arrangement can also provide a compressive force between the implant and the facets to promote adhesion and/or osteoincorporation of the implant with the articular surfaces of the facets. Any appropriate anchoring arrangement, such as those described herein, may be used. The surgical site is then closed, cleaned and dressed.

The foregoing merely illustrates the principles of the invention. Various modifications and alterations to the described embodiments will be apparent to those skilled in the art in view of the teachings herein. It will thus be appreciated that those skilled in the art will be able to devise numerous techniques which, although not explicitly described herein, embody the principles of the invention and are thus within the spirit and scope of the invention. All patents, patent applications, and other publications cited herein are incorporated herein by reference in their entireties.

What is claimed is:

1. A device for treating spinal disorders by inhibiting movement at a facet joint, the device comprising:
   an implant having a first face and a second face, and an aperture extending from the first face to the second face, wherein the implant is dimensioned to fit substantially within a joint capsule of the facet joint and wherein an entire periphery of the implant has a thickness that is greater than a thickness measured from the first face to the second face of a central region of the implant;
   a fastener in operation extending through the aperture of the implant and configured to maintain the first face in a fixed position relative to an adjacent articular surface of a first facet, and to maintain the second face in a fixed position relative to an adjacent articular surface of a second facet, the fastener with at least one enlarged structure adapted to abut a non-articular surface of the first or second facet for providing a compressive force between the implant and the facets.

2. The device of claim 1, wherein the implant has a thickness that is approximately the same as a normal anatomic spacing between the first and second facets of the facet joint.

3. The device of claim 1, wherein a shape of the first face of the implant is configured to conform to the articular surface of the first facet of the facet joint, and the second face of the implant is configured to conform to the articular surface of the second facet of the facet joint.

4. The device of claim 1, wherein the implant comprises at least one of a polymer, polyetheretherketone (PEEK), polyetherketoneketone (PEKK), polyethylene, a ceramic, zirconia, alumina, silicon nitride, a metal, titanium, a titanium alloy, cobalt chromium, or a stainless steel.

5. The device of claim 1, wherein the implant comprises at least one of an autograft material or an allograft material.

6. The device of claim 1, wherein each of the first face and the second face comprises a roughened surface.

7. The device of claim 1, wherein each of the first face and the second face comprises a porous surface.

8. The device of claim 1, wherein the implant has an average thickness that is between about 0.5 mm and about 3 mm.

9. The device of claim 1, wherein the implant has an average thickness that is between about 1 mm and about 2 mm.

10. The device of claim 1, wherein the implant has an average lateral dimension that is between about 5 mm and about 25 mm.

11. The device of claim 1, wherein the implant has an average lateral dimension that is between about 10 mm and about 20 mm.

12. The device of claim 1, wherein the device is configured to be bonded to the articular surfaces of the first and second facets using at least one of an adhesive or a sealant.

13. The device of claim 1, wherein the fastener comprises a threaded retainer.

14. The device of claim 13, wherein the enlarged structure is a threaded nut.

15. The device of claim 1, wherein the fastener comprises at least one of a bolt or a screw.

16. The device of claim 1, wherein the fastener comprises a bone screw.

17. The device of claim 1, wherein the enlarged structure is a flange.

18. The device of claim 1, further comprising a nut coupled to a portion of the fastener opposite the enlarged structure, wherein the nut can move along the fastener to abut a non-articular surface of the first or second facet to provide the compressive force between the implant and the facets.

19. The device of claim 1, wherein the first face and the second face of the implant are concave.

20. A device for treating spinal disorders by inhibiting movement at a facet joint, the device comprising:
   an implant having a first face and a second face, and an aperture extending from the first face to the second face, wherein the implant is dimensioned to fit substantially within a joint capsule of the facet joint;
   a fastener in operation extending through the aperture of the implant and configured to maintain the first face in a fixed position relative to an adjacent articular surface of a first facet, and to maintain the second face in a fixed position relative to an adjacent articular surface of a second facet, the fastener with at least one enlarged structure adapted to abut a non-articular surface of the first or second facet for providing a compressive force between the implant and the facets, wherein the fastener comprises a threaded retainer that is curved along a primary axis thereof.

* * * * *